(12) United States Patent
Fares et al.

(10) Patent No.: US 8,158,136 B2
(45) Date of Patent: Apr. 17, 2012

(54) EMULSIFICATION SYSTEM FOR USE IN COSMETICS

(75) Inventors: Hani Fares, Somerset, NJ (US); Rita Marie Grosso, Morris Plains, NJ (US); Sidney Peter Foltis, Nutley, NJ (US); Isabelle Hansenne, Westfield, NJ (US)

(73) Assignee: L'Oréal (FR)

( * ) Notice: Subject to any disclaimer, the term of this patent is extended or adjusted under 35 U.S.C. 154(b) by 1139 days.

(21) Appl. No.: 10/920,615

(22) Filed: Aug. 18, 2004

(65) Prior Publication Data

US 2006/0039936 A1   Feb. 23, 2006

(51) Int. Cl.
*A61K 8/02* (2006.01)
*A61K 9/00* (2006.01)
(52) U.S. Cl. .................................. 424/401; 424/400
(58) Field of Classification Search .................. 424/400, 424/401
See application file for complete search history.

(56) References Cited

U.S. PATENT DOCUMENTS

| | | | |
|---|---|---|---|
| 6,013,270 | A | 1/2000 | Hargraves et al. |
| 6,071,501 | A | 6/2000 | Robinson |
| 6,174,533 | B1 | 1/2001 | SaNogueira, Jr. et al. |
| 6,551,604 | B1 | 4/2003 | Beck et al. |
| 2002/0035046 | A1 | 3/2002 | Lukenbach et al. |
| 2002/0039561 | A1 | 4/2002 | Doughty et al. |
| 2003/0199584 | A1 | 10/2003 | Ahluwalia et al. |
| 2003/0235539 | A1 | 12/2003 | Mongiat et al. |

FOREIGN PATENT DOCUMENTS

| | | |
|---|---|---|
| EP | 0 794 764 A | 9/1997 |
| EP | 1 371 355 A1 | 12/2003 |
| EP | 1679063 | 7/2006 |
| WO | WO 9616636 A1 * | 6/1996 |
| WO | WO 03/063814 A1 | 8/2003 |
| WO | WO 03/075875 A1 | 9/2003 |
| WO | WO 03/086341 A2 | 10/2003 |
| WO | WO 2004/006878 A1 | 1/2004 |

OTHER PUBLICATIONS

European Search Report, EP 05 25 4363, Dated Dec. 2, 2005.
Fiche d'identite-Precision Rectifiance Intense.
Uniqema, Product Catalog, EV 2025/105-4, O/W Body Butter.
Uniqema, Product Catalog, CP 2089, Emollient Facial Washing Lotion.
Uniqema, Product Catalog, F41-5-2, O/W Sun Protection Cream.
Uniqema, Product Catalog, EV 1033-40/3, O/W AHA Cream.
Uniqema, Product Catalog, 5051*4, W/O/W Sunscreen Cream.
Fiche d'identite, Proctor & Gamble, Oil of Olay-Total Effects with Vitaniacin.

* cited by examiner

*Primary Examiner* — Samira Jean-Louis
(74) *Attorney, Agent, or Firm* — Lerner, David, Littenberg, Krumholz & Mentlik, LLP

(57) ABSTRACT

Disclosed are cosmetic compositions containing water, at least one non-polar and/or polar oil, and an emulsification system comprising a polyoxyethylene oxide C12-C24 fatty acid ester; a sucrose fatty acid ester of vegetable origin, and a glyceryl and/or sorbitan C12-C24 fatty acid ester, and methods of making and using the compositions.

49 Claims, No Drawings

EMULSIFICATION SYSTEM FOR USE IN COSMETICS

BACKGROUND OF THE INVENTION

Cosmetic compositions in the form of emulsions may enhance comfort of use, particularly in terms of softness and emollience. Such emulsions include oil-in-water (O/W) emulsions, which are composed of a continuous aqueous dispersing phase and a non-continuous oily dispersed phase, and water-in-oil (W/O) emulsions, which are composed of a continuous oily dispersing phase and a non-continuous aqueous dispersed phase. Cosmetic emulsions are generally stabilized by appropriate emulsifying surfactants that by virtue of their amphiphilic structure, reside at the oil/water interface and thus stabilize the dispersed droplets. Oils of varying and even opposite polarities, including mixtures of oils of different polarities, may be used in cosmetic emulsions. To emulsify a mixture of polar and non-polar oils, a mixture of high and low HLB surfactants is typically employed. However, the same mixture of surfactants will not necessarily emulsify either oil alone. Thus, surfactant or emulsification systems with more versatility would be desirable.

SUMMARY OF THE INVENTION

Cosmetic emulsions contain oil phases that vary in terms of polarity. Typically, no one surfactant or mixture of surfactants has been found universally suitable to emulsify an oil phase, regardless of the polarity. Conventional wisdom suggests mixing high and low HLB surfactants in order to emulsify oils of different polarities. Applicants discovered that not all such mixtures of high and low HLB surfactants have the versatility to emulsify a polar oil contained in one composition and a non-polar oil contained in a separate composition. For example, the mixture of polysorbate 80 (a high HLB surfactant) and sorbitan stearate and sucrose cocoate (both low HLB surfactants) failed to emulsify the non-polar oil polyisobutene. Likewise, a mixture of glyceryl stearate (a low HLB surfactant) and PEG 75 stearate (a high HLB surfactant) also failed to emulsify polyisobutene. Applicants have discovered an emulsification system that contains specific surfactants each present in specific amounts that provides for relatively universal emulsifying properties, enabling it to emulsify not only mixtures of polar and non-polar oils, but either polar or non-polar oils as well, without sacrificing aesthetic appeal or desired particle size.

Accordingly, a first aspect of the present invention is directed to a cosmetic composition, comprising water, at least one non-polar and/or polar oil, and an emulsification system comprising a polyoxyethylene oxide C12-C24 fatty acid ester; a sucrose fatty acid ester of vegetable origin, and a glyceryl and/or sorbitan C12-C24 fatty acid ester, wherein the polyoxyethylene oxide C12-24 fatty acid ester and the sucrose fatty acid ester of vegetable origin are present in a ratio of at least about 5, and wherein said glyceryl and/or sorbitan C12-24 fatty acid ester is present in an amount of least about 2%, said ratio and said amount being based on the total weight of said composition.

A second aspect of the present invention is directed to a method of applying make-up to keratinous tissue (e.g., the skin or scalp), comprising the cosmetic composition of the present invention to the tissue. These and other aspects of the present invention are described below.

DETAILED DESCRIPTION OF THE INVENTION

The cosmetic compositions according to the invention are in the form of emulsions, e.g., oil-in-water (O/W) or water-in-oil (W/O) or multiple (W/O/W or O/W/O). In preferred embodiments, the emulsion is an O/W emulsion. The proportion of water and cosmetically acceptable ingredient(s) soluble in water (collectively an "aqueous phase") generally ranges from about 30 to about 95% by weight, and preferably from about 50 to about 85%, based on the total weight of the composition. The proportion of the oil(s) and the cosmetically acceptable ingredient(s) soluble therein (collectively the "oil phase") in the emulsion generally ranges from about 5% to about 70% by weight and preferably from about 15% to about 50% by weight relative to the total weight of the composition. The cosmetic compositions of the present invention are typically in the form of a white or colored cream, an ointment, milk, a lotion or a serum.

The emulsification system of the present invention contains a mixture of specific high HLB (e.g., an HLB of at least 10, and more typically from about 10-15) and low HLB surfactants (e.g., generally from about 4-6). The polyoxyethylene oxide portion of the C12-C24 fatty acid ester (including both unsaturated and saturated acids) is a polyethylene glycol (PEG) generally having about 50 to about 150, and preferably about 75 to about 100 moles or units of PEG, e.g., PEG 75 and PEG 100. Thus, representative esters include PEG 75 stearate, PEG 100 stearate, PEG 75 oleate, PEG 100 oleate, PEG 75 palmitate and PEG 100 palmitate. Representative examples of sucrose fatty acid esters of vegetable origin (e.g., soybean, peanut, palm kernel, palm, olive, corn and coconut) include sucrose cocoate and sucrose ricinoleate. The C12-C24 glyceryl and sorbitan fatty acid esters (including both unsaturated and saturated acids) include glyceryl oleate, glyceryl stearate, glyceryl palmitate, sorbitan oleate, sorbitan stearate and sorbitan palmitate.

Preferred emulsification systems include mixtures of PEG 75 or PEG 100 stearate, sucrose cocoate, and glyceryl and/or sorbitan stearate. Thus, these embodiments include the following mixtures: PEG 75 stearate, sucrose cocoate and glyceryl stearate; PEG 100 stearate, sucrose cocoate and glyceryl stearate; PEG 75 stearate, sucrose cocoate and sorbitan stearate; and PEG 100 stearate, sucrose cocoate and sorbitan stearate. In various preferred embodiments, both glyceryl and sorbitan fatty acid esters are present. In these embodiments, the fatty acid ester may be the same or different. Examples of such emulsification systems include the following: PEG 75 stearate, sucrose cocoate, sorbitan stearate and glyceryl stearate; and PEG 100 stearate, sucrose cocoate, sorbitan stearate and glyceryl stearate.

The term "system/" is not intended to mean that the surfactants are pre-mixed or take any particular form with respect to the cosmetic composition as a whole. They may be added together or separately or in sub-combinations. For example, in embodiments where both sorbitan and glyceryl fatty acid esters are present, along with sucrose cocoate and PEG 75 stearate, the combinations of sorbitan stearate and sucrose cocoate, and the glyceryl stearate and the PEG 75 stearate may be conveniently obtained commercially from Uniqema (Arlatone 2121) and Gattefosse (Gelot 64), respectively.

The emulsification system is present in the cosmetic composition in an amount effective to emulsify the oil of choice. In general, the amount of the emulsification (i.e., the additive amount of each of the surfactants contained in the system) ranges from about 2.0% to about 15%, and preferably from about 3% to about 7%, based on the total weight of the cosmetic composition. The polyoxyethylene oxide C12-C24 fatty acid ester is present in an amount generally ranging from about 0.25% to about 6%, and preferably from about 1% to about 3%. The sucrose fatty acid ester is present in an amount generally ranging from about 0.05% to about 0.5%, and preferably from about 0.1% to about 0.3%.

The ratio of the polyoxyethylene oxide C12-C24 fatty acid ester to the sucrose fatty acid ester is at least about 5, e.g., including but not limited to 4.5, 4.6, 4.7, 4.8, 4.9 and 5.0, and typically ranges from about 5 to about 12, e.g., 5, 5.25, 5.5, 5.75, 6, 6.25, 6.5, 6.75, 7, 7.25, 7.5, 7.75, 8, 8.25, 8.5, 8.75, 9, 9.25, 9.5, 9.75, 10, 10.25, 10.5, 10.75, 11, 11.25, 11.5, 11.75 and 12. Ratios higher than about 12, e.g., 13, may also be useful.

The glyceryl and/or sorbitan fatty acid ester is present in an amount of at least about 2%, generally from 2% to about 9%, and preferably from about 3% to about 7%. In embodiments where both glyceryl and sorbitan fatty acid esters are present, the combination of the glyceryl C12-C24 fatty acid ester and the polyoxyethylene oxide C12-C24 fatty acid ester is present in an amount generally ranging from about 3% to about 10%, and preferably from about 4% to about 8%. The combination of the sucrose fatty acid ester and the sorbitan fatty acid ester is present in an amount generally ranging from about 0.5% to about 1.5%, and preferably from about 0.7% to about 1.2%. All such percentages are based on weight compared to the total weight of the cosmetic composition. Generally, the emulsification system is effective in maintaining an emulsion having particle sizes ranging from about 0.5 to about 30 microns ($\mu$). The emulsions may remain stable for prolonged periods of time.

The emulsification system may contain other emulsifying agents or surfactants, e.g., cetearyl alcohol, cetyl alcohol, Ceteth-20 and Ceteareth-20, provided however, that their presence does not sacrifice or otherwise detract from the primary benefit of the system, which is to emulsify an oil regardless of the polarity.

Cosmetic compositions of the present invention contain one or more polar oils, one or more non-polar oils, or a mixture of the polar and non-polar oils. For example, the at least one polar oil useful in the invention may be chosen from:

hydrocarbon-based plant oils with a high content of triglycerides comprising fatty acid esters of glycerol in which the fatty acids may have varied chain lengths from $C_4$ to $C_{24}$, these chains possibly being chosen from linear and branched, and saturated and unsaturated chains; these oils are chosen from, for example, wheat germ oil, corn oil, sunflower oil, karite butter, castor oil, sweet almond oil, macadamia oil, apricot oil, soybean oil, cotton oil, alfalfa oil, poppy oil, pumpkin oil, sesame oil, marrow oil, rapeseed oil, avocado oil, hazelnut oil, grape seed oil, blackcurrant seed oil, evening primrose oil, millet oil, barley oil, quinoa oil, olive oil, rye oil, safflower oil, candlenut oil, passion flower oil and musk rose oil; or alternatively caprylic/capric acid triglycerides such as those sold by Stearineries Dubois or those sold under the names Miglyol 810, 812 and 818 by Dynamit Nobel;

synthetic oils or esters of formula $R_5COOR_6$ in which $R_5$ is chosen from linear and branched fatty acid residues containing from 1 to 40 carbon atoms and $R_6$ is chosen from, for example, a hydrocarbon-based chain containing from 1 to 40 carbon atoms, on condition that $R_5+R_6>10$, such as, for example, purcellin oil (cetostearyl octanoate), isononyl isononanoate, $C_{12}$-$C_{15}$ alkyl benzoates, isopropyl myristate, 2-ethylhexyl palmitate, isostearyl isostearate and alkyl or polyalkyl octanoates, decanoates or ricinoleates; hydroxylated esters such as isostearyl lactate and diisostearyl malate; and pentaerythritol esters;

synthetic ethers containing from 10 to 40 carbon atoms;
$C_8$ to $C_{26}$ fatty alcohols such as oleyl alcohol; and
$C_8$ to $C_{26}$ fatty acids such as oleic acid, linolenic acid or linoleic acid.

In preferred embodiments, the polar oil comprises an alkyl benzoate, such as a C12-C15 alkyl benzoate.

The at least one non-polar oil according to the invention may include a hydrocarbon chosen from linear and branched, volatile and non-volatile hydrocarbons of synthetic and mineral origin, such as volatile liquid paraffins (such as isoparaffins and isododecane) or non-volatile liquid paraffins and derivatives thereof, liquid petrolatum, liquid lanolin, polydecenes, hydrogenated polyisobutene such as Parleam®, and squalane, silicone oils, polydimethylsiloxanes and phenylsilicones. In preferred embodiments, the non-polar oil is a polyisobutene e.g., a hydrogenated polyisobutene.

The oil phase may additionally contain at least one non-volatile oil chosen from, for example, hydrocarbon-based oils of mineral, plant and synthetic origin, synthetic esters or ethers, silicone oils and mixtures thereof.

The cosmetic compositions of the present invention may further comprise one or more dermatological active agents e.g., agents capable of treating or preventing any sign of ageing of the skin. The active agents may be chosen, for example, from moisturizers, free-radical scavengers, keratolytic agents, vitamins, anti-elastase and anti-collagenase agents, peptides, fatty acid derivatives, steroids, trace elements, bleaching agents, extracts of algae and of planktons, sunscreens, enzymes and coenzymes, flavonoids and ceramides, $\alpha$-hydroxy acids and mixtures thereof.

Useful moisturizers include sodium lactate; polyols, and in particular glycerol, sorbitol and polyethylene glycols; mannitol; amino acids; hyaluronic acid; lanolin; urea and mixtures containing urea, such as NMF ("Natural Moisturizing Factor"); petroleum jelly; and mixtures thereof.

Useful free-radical scavengers include phosphonic acid derivatives such as ethylenediaminetetra(methylenephosphonic acid), hexamethylenediaminetetra(methylenephosphonic acid), diethylenetriamin.epenta(methylenephosphonic acid), and their salts and in particular their sodium salts, such as pentasodium ethylenediaminetetra(methylenephosphonic acid); ethylenediaminetetraacetic acid and its salts such as sodium salt; guanosine; superoxydismutase; tocopherol (vitamin E) and its derivatives (acetate); ethoxyquine; lactoferrin; lactoperoxidase and nitroxide derivatives; superoxide dismutases; glutathione peroxidase; plant extracts with free-radical-scavenging activity, such as the aqueous extract of wheat germ sold by the company Silab under the reference Detoxiline; and mixtures thereof.

Useful keratolytic agents include a-hydroxy acids, especially acids derived from fruit, for instance glycolic acid, lactic acid, malic acid, citric acid, tartaric acid and mandelic acid, derivatives thereof and mixtures thereof; $\beta$-hydroxy acids, for instance salicylic acid and its derivatives such as 5-n-octanoylsalicylic acid or 5-n-dodecanoylsalicylic acid; $\alpha$-keto acids, for instance ascorbic acid or vitamin C and its derivatives such as its salts, for instance sodium ascorbate, magnesium ascorbyl phosphate or sodium ascorbyl phosphate; its esters, for instance ascorbyl acetate, ascorbyl palmitate and ascorbyl propionate, or its sugars, for instance glycosylated ascorbic acid, and mixtures thereof; $\beta$-keto acids; retinoids, for instance retinol (vitamin A) and its esters, retinal, retinoic acid and its derivatives, and also the retinoids described in documents FR-A-2,570,377, EP-A-199 636, EP-A-325-540 and EP-A-402 072; and mixtures thereof.

Useful vitamins, in addition to vitamins A, E and C indicated above, include vitamin B3 (or vitamin PP or niacinamide), vitamin B5 (or panthenol), vitamin D, vitamin F, derivatives, analogues and precursors of these vitamins and also those of vitamins A, E and C, for instance lycopenes or carotenes that are precursors of vitamin A, and mixtures thereof. Vitamin B3 derivatives include nicotinic acid esters, such as tocopherol nicotinate; amides derived from niacinamide by substitution of the hydrogen groups of —CONH$_2$; products of reaction with carboxylic acids and amino acids; esters of nicotinyl alcohol and of carboxylic acids such as acetic acid, salicylic acid, glycolic acid or palmitic acid. Mention may also be made of the following derivatives: 2-chloronicotinamide, 6-methylnicotinamide, 6-aminonicotinamide, N-methylnicotinamide, N,N-dimethylnicotinamide, N-(hydroxymethyl)nicotinamide, quinolinic acid imide, nicotinanilide, N-benzylnicotinamide, N-ethylnicotinamide, nifenazone, nicotinaldehyde, isonicotinic acid, methylisonicotinic acid, thionicotinamide, nialamide, 2-mercaptonicotinic acid, nicomol and niaprazine. Other vitamin B3 derivatives which may also be mentioned include its mineral salts such as the chlorides, bromides, iodides and carbonates, and its organic salts, such as the salts obtained by reaction with carboxylic acids such as acetate, salicylate, glycolate, lactate, malate, citrate, mandelate and tartrate.

As vitamin B5, it is also possible to use panthenol or panthenyl alcohol or 2,4-dihydroxy-N(3-hydroxypropyl)-3,3-dimethylbutanamide, in its various forms: D-panthenol, DL-panthenol, and its derivatives and analogues, such as calcium pantothenate, pantethine, pantotheine, ethyl panthenyl ether, pangamic acid, pyridoxine and pantoyllactose, and natural compounds containing them such as royal jelly.

As vitamin D, mention may be made of 1α, 25-dihydroxy vitamin D3 and its analogues, and also vitamin D analogues, such as those described in document WO-A-00/26167, such as, for example: 3-hydroxymethyl-5-{2-[3-(5-hydroxy-5- or 6-methylhexyl)-phenyl]-vinyl)-phenol, 3-[3-(5-hydroxy-1,5-dimethyl-hexyl)-phenoxymethyl]-5-hydroxymethyl-phenol, 6-[3-(3,4-bis-hydroxymethyl-benzyloxy)-phenyl]-2-methyl-hepta-3,5-dien-2-ol, 6-[3-(3,4-bis-hydroxymethyl-benzyloxy)-phenyl]-2-methyl-hexan-2-ol, 6-[3-(3,4-bis-hydroxymethyl-phenoxymethyl) -phenyl]-2-methyl-heptan-2-ol, 7-[3-(3,4-bis-hydroxymethyl -phenoxymethyl)-phenyl]-3-ethyl-octan-3-ol, 5-{2-[4-(5-hydroxy-5-methyl-hexyl)-phenyl]-vinyl or -ethyl}-benzene-1,3-diol, 5-{2-[3- or 4-(6-hydroxy-6-methyl-heptyl)phenyl]vinyl}-benzene-1,3-diol, 5-{2-[3- or 4-(6-hydroxy-6-methyl-heptyl) -phenyl] ethyl -benzene-1,3-diol, 2-hydroxymethyl-4-{2-[3- or 4-(5-hydroxy-5-methylhexyl)-phenyl]-vinyl-phenol, 2-hydroxymethyl-4-{2-[3- or 4-(6-hydroxy-6-methylheptyl)-phenyl]-vinyl}-phenol, 2-hydroxymethyl-4-{2-[3- or 4-(5-hydroxy-5-methylheptyl)-phenyl]-ethyl}-phenol, 2-hydroxymethyl-4-{2-[3- or 4-(6-hydroxy-6-methylheptyl)-phenyl]-ethyl}-phenol, 2-hydroxymethyl-5-(2-[4-(5-hydroxy-5-methyl-hexyl)phenyl]-vinyl-phenol, 6-[3-(3,4-bis-hydroxymethyl-benzyloxy)-phenyl-1,2-methyl-heptan-2-ol, 4-[3-(5-hydroxy-1,5-dimethyl-hexyl)-phenoxymethyl]2-hydroxymethyl-p-phenol, 6-[3- or 4-[2-(3,4-bis-hydroxymethyl-phenyl)-vinyl]phenyl}-2-methyl-hexan-2-ol, 7-{4-[2-(3,4-bis-hydroxymethyl-phenyl)-vinyl]phenyl}-2-methyl-heptan-2-ol, 5-{2-[3-(6-hydroxy-6-methyl-heptyl)-phenyl]-1-methylvinyl-benzene-1, 3-diol, 5-{2-[3-(5-hydroxy-5-methyl-hexyl)-phenyl]-vinyl}benzene-1,3-diol, 5-[3-(6-hydroxy-6-methyl-heptyl)-phenoxymethyl]benzene-1,3-diol, 5-{2-[3-(7-hydroxy-7-methyl-oct-1-enyl)-phenyl]vinyl}-benzene-1,3-diol, 5-{2-[3-(7-hydroxy-7-methyl-octyl)-phenyl]-vinyl]benzene-1,3-diol, 4-{2-[3-(6-hydroxy-6-methyl-heptyl)-phenyl]-vinyl)benzene-1,2-diol, 3-{2-[3-(6-hydroxy-6-methyl-heptyl)-phenyl]-vinyl}phenol, 6-{3-[2-(3,5-bis-hydroxymethyl-phenyl)-vinyl]phenyl}-2-methyl-hexan-2-ol, 3-{2-[3-(7-hydroxy-7-methyl-octyl)-phenyl]-vinyl}phenol, 7-(3-[2-(3,5-bis-hydroxymethyl-phenyl)-vinyl]phenyl-2-methyl -heptan-2-ol, 7-{3-[2-(3,4-bis-hydroxymethyl-phenyl) -vinyl]phenyl}-2-methyl-heptan-2-ol, 7-{3-[2-(4-hydroxymethyl -phenyl)-vinyl]-phenyl}2-methyl-heptan-2-ol, 4-{2-[3-(7-hydroxy-7-methyl-oct-1-enyl)-phenyl]vinyl}-benzene-1,2-diol, 7-[3-(3,4-bis-hydroxymethyl-phenylethynyl)-phenyl]2-methyl-heptan-2-ol, 5-{2-[3-(6-hydroxy-6-methyl-hept-1-enyl) -phenyl]vinyl)-benzene-1,3-diol, 5-{2-[3-(7-ethyl-7-hydroxy-non-1-enyl) -phenyl]vinyl)-benzene-1,3-diol, 5-{2-[3-(7-hydroxy-1-methoxy-1,7-dimethyl-octyl)phenyl]-vinyl-benzene-1,3-diol, 5-{2-[3-(6-hydroxy-1-methoxy-1,6-dimethyl-heptyl)phenyl]-vinyl}-benzene-1,3-diol, 5-{2-[3-(5-hydroxypentyl)-phenyl]-vinyl-benzene-1,3-diol, 5-{2-[3-(5-hydroxy-6-methyl-heptyl)-phenyl]-vinyl}benzene-1,3-diol, 5-{2-[3-(6-hydroxy-7-methyl-octyl)-phenyl]-vinyl)benzene-1,3-diol, 5-{2-[3-(5-hydroxy-6-methyl -hept-1-enyl)-phenyl]vinyl}-benzene-1,3-diol, 5-{2-[3-(6-hydroxy-7-methyl-oct-1-enyl)-phenyl]vinyl}-benzene-1,3-diol, 5-{2-[3-(1,6-dihydroxy-1,6-dimethyl-heptyl)-phenyl]vinyl}-benzene-1,3-diol, and 5-(2-[3-(6-hydroxy-1,6-dimethyl-hept-1-enyl)-phenyl]vinyl}-benzene-1,3-diol.

Vitamin F is a mixture of essential fatty acids, that is to say of unsaturated acids containing at least one double bond, such as linoleic acid or 9,12-octadecadienoic acid, and its stereoisomers, linolenic acid in a form (9,12,15-octadecatrienoic acid) or the gamma form (6,9,12-octadecatrienoic acid) and stereoisomers thereof, arachidonic acid or 5,8,11,14-eicosatetraenoic acid and its stereoisomers.

Vitamin F or analogues thereof such as mixtures of unsaturated acids containing at least one double bond and especially mixtures of linoleic acid, of linolenic acid and of arachidonic acid, or compounds containing them and especially oils of plant origin containing them such as, for example, jojoba oil, may be used in the composition of the present invention.

Useful anti-elastase agents include peptide derivatives and especially peptides from leguminous seeds such as those sold by Laboratoires Seriobiologiques de Nancy under the reference Parelastyl; the N-acylamino amide derivatives described in patent application FR-A-2,180,033, such as, for example, ethyl {2-[acetyl(3-trifluoromethylphenyl)amino]-3-methylbutyrylamino}acetate and {2-[acetyl-(3-trifluoromethylphenyl)amino]-3-methylbutyrylaminol acetic acid, and mixtures thereof. Anti-collagenase agents that may be mentioned include metalloprotease inhibitors, such as ethylenediamine acid (EDTA) and cysteine, and mixtures thereof.

Useful peptides include proteins (wheat or soybean protein), hydrolysates thereof, for instance those sold by the company Silab under the reference Tensine, and mixtures thereof.

Useful fatty acid derivatives include polyunsaturated phospholipids including the essential fatty acid phospholipids from octopus, and mixtures thereof.

Useful steroids include DHEA or dehydroepiandrosterone, its biological precursors, its metabolites, and mixtures thereof. The expression "biological precursors" of DHEA especially means Δ5-pregnenolone, 17α-hydroxypregnenolone and 17α-hydroxypregnenolone sulphate. The expression "DHEA derivatives" means both its metabolic derivatives and its chemical derivatives. Metabolic derivatives that may especially be mentioned include Δ5-androstene-3,17-diol and especially 5-androstene-3β,17β-diol, Δ4-androstene-3,17-dione, 7-hydroxy DHEA (7a-hydroxy DHEA or 7β-hydroxy DHEA) and 7-keto-DHEA which is itself a metabolite of 7β-hydroxy DHEA. A preferred group is dehydroepiandrosterone, 5-pregnenolone, 17-hydroxypregnenolone, 17-hydroxypregnenolone sulphate, 5-androstene- 3,17-diol, 4-androstene-3,17-dione, 7-hydroxy DHEA, 7-hydroxy DHEA, 7-keto-DHEA, and mixtures thereof.

Useful trace elements include copper, zinc, selenium, iron, magnesium and manganese, and mixtures thereof.

Useful bleaching agents include any compound for treating or preventing age marks, that is to say any depigmenting compound which acts directly on the vitality of the epidermal melanocytes in which melanogenesis takes place and/or which interferes with one of the steps in the biosynthesis of melanin either by inhibiting one of the enzymes involved in melanogenesis or by becoming intercalated as a structural analogue of one of the chemical compounds in the synthetic chain of melanin, which chain may thus be blocked and bring about the depigmentation. Bleaching active agents that may be mentioned, for example, include kojic acid and its derivatives, hydroquinone and its derivatives such as arbutin and its esters; ellagic acid and its derivatives; plant extracts, and especially extracts of licorice, of mulberry or of scutellaria; glutathione and its precursors; cysteine and its precursors; the compounds derived from aminophenol that are described in document WO-A-99/10318, such as, especially, N-ethyloxycarbonyl-4-aminophenol, N-ethyloxycarbonyl-O-ethyloxycarbonyl-4-aminophenol, N-cholesteryloxycarbonyl-4-aminophenol and N-ethylaminocarbonyl-4-aminophenol; and mixtures of these compounds.

Useful extracts of algae include extracts of red or brown algae and, for example, the extract of brown algae from the Laminaria family, for instance the extracts from the species Laminaria digitata, and more particularly the product sold by the company CODIF under the name Phycosaccharides, which is a concentrated solution of an oligosaccharide obtained by controlled enzymatic depolymerization of membrane polysaccharides of a brown alga. It comprises a sequence of two uric acids, namely mannuronic acid and guluronic acid.

Useful extracts of planktons include plankton in aqueous dispersion (CTFA name: Vitreoscilla Ferment) sold under the name Mexoryl SAH by the company Chimex.

The cosmetic compositions of this invention may also comprise sunscreens which are chemical absorbers actually absorb harmful ultraviolet radiation. It is well known that chemical absorbers are classified, depending on the type of radiation they protect against, as either UV-A or UV-B absorbers. UV-A absorbers generally absorb radiation in the 320 to 400 nm region of the ultraviolet spectrum. UV-A absorbers include anthranilates, benzophenones, and dibenzoyl methanes. UV-B absorbers generally absorb radiation in the 280 to 320 nm region of the ultraviolet spectrum. UV-B absorbers include p-aminobenzoic acid derivatives, camphor derivatives, cinnamates, and salicylates.

Classifying the chemical absorbers generally as UV-A or UV-B absorbers is accepted within the industry. However, a more precise classification is one based upon the chemical properties of the sunscreens. There are eight major classifications of sunscreen chemical properties that are discussed at length in "*Sunscreens—Development, Evaluation and Regulatory Aspects,*" by N. Shaath et al., 2nd. Edition, pages 269-273, Marcel Dekker, Inc. (1997).

The sunscreens useful in the present invention typically comprise chemical absorbers, but may also comprise physical blockers. Exemplary sunscreens which may be formulated into the compositions of the present invention are chemical absorbers such as p-aminobenzoic acid derivatives, anthranilates, benzophenones, camphor derivatives, cinnamic derivatives, dibenzoyl methanes (such as avobenzone also known as Parsol®1789), diphenylacrylate derivatives, salicylic derivatives, triazine derivatives, benzimidazole compounds, bis-benzoazolyl derivatives, methylene bis-(hydroxyphenylbenzotriazole) compounds, the sunscreen polymers and silicones, or mixtures thereof. These are variously described in U.S. Pat. Nos. 2,463,264, 4,367,390, 5,166,355 and 5,237,071 and in EP 863,145, EP 517,104, EP 570,838, EP 796,851, EP 775,698, EP 878,469, EP 933,376, EP 893,119, EP 669,323, GB 2,303,549, DE 1,972,184 and WO 93/04665. Also exemplary of the sunscreens which may be formulated into the compositions of this invention are physical blockers such as cerium oxides, chromium oxides, cobalt oxides, iron oxides, red petrolatum, silicone-treated titanium dioxide, titanium dioxide, zinc oxide, and/or zirconium oxide, or mixtures thereof.

A wide variety of sunscreens is described in U.S. Pat. Nos. 5,087,445 and 5,073,372, and Chapter VIII of Cosmetics and Science and Technology (1957) by Segarin et al., pages 189 et seq.

Sunscreens which may be formulated into the compositions of the instant invention are those selected from among: aminobenzoic acid, amyldimethyl PABA, cinoxate, diethanolamine p-methoxycinnamate, digalloyl trioleate, dioxybenzone, 2-ethoxyethyl p-methoxycinnamate, ethyl 4-bis (hydroxypropyl)aminobenzoate, 2-ethylhexyl-2-cyano-3,3-diphenylacrylate, ethylhexyl p-methoxycinnamate, 2-ethylhexyl salicylate, glyceryl aminobenzoate, homomenthyl salicylate, homosalate, 3-imidazol-4-ylacrylic acid and ethyl ester, methyl anthranilate, octyldimethyl PABA, 2-phenylbenzimidazole-5-sulfonic acid and salts, red petrolatum, sulisobenzone, titanium dioxide, triethanolamine salicylate, N,N,N-trimethyl-4-(2-oxoborn-3-ylidene methyl)anillinium methyl sulfate, and mixtures thereof.

Sunscreens active in the UV-A and/or UV-B range can also include:
 p-aminobenzoic acid,
 oxyethylene (25 mol) p-aminobenzoate,
 2-ethylhexyl p-dimethylaminobenzoate,
 ethyl N-oxypropylene p-aminobenzoate,
 glycerol p-aminobenzoate,
 4-isopropylbenzyl salicylate,
 2-ethylhexyl 4-methoxycinnamate,
 methyl diisopropylcinnamate,
 isoamyl 4-methoxycinnamate,
 diethanolamine 4-methoxycinnamate,
 3-(4'-trimethylammunium)-benzyliden-bornan-2-one methylsulfate,
 2-hydroxy-4-methoxybenzophenone,
 2-hydroxy-4-methoxybenzophenone-5-sulfonate,
 2,4-dihydroxybenzophenone,
 2,2',4,4'-tetrahydroxybenzophenone,
 2,2'-dihydroxy-4,4'dimethoxybenzophenone,
 2-hydroxy-4-n-octoxybenzophenone,
 2-hydroxy-4-methoxy-4'-methoxybenzophenone,
 -(2-oxoborn-3-ylidene)-tolyl-4-sulfonic acid and soluble salts thereof,
 3-(4'-sulfo)benzyliden-bornan-2-one and soluble salts thereof,
 3-(4'methylbenzylidene)-d,1-camphor,
 3-benzylidene-d,1-camphor,
 benzene 1,4-di(3-methylidene-10-camphosulfonic) acid and salts thereof (the product Mexoryl SX described in U.S. Pat. No. 4,585,597),
 urocanic acid,
 2,4,6-tris[p-(2'-ethylhexyl-1'-oxycarbonyl)-anilino]-1,3,5-triazine,
 2-[(p-(tertiobutylamido)anilino]-4,6-bis-[(p-(2'-ethylhexyl-1'-oxycarbonyl)anilino]-1,3,5-triazine, 2,4-bis{[4-(2-ethyl-hexyloxy)]-2-hydroxy]-phenyl}-6-(4-methoxy-phenyl)-1,3,5-triazine ("TINOSORB S" marketed by Ciba), the polymer of N-(2,4)-[(2-oxoborn-3-yliden)methyl]benzyl]-acrylamide, 1,4-bisbenzimidazolyl-phenylen-3,3',5,5'-tetrasulfonic acid and salts thereof, the benzalmalonate-substituted polyorganosiloxanes, the benzotriazole-substituted polyorganosiloxanes (Drometrizole Trisiloxane), dispersed 2,2'-methylene-bis-[6-(2H-benzotriazol-2-yl)-4-(1,1,3,3-tetramethylbutyl)phenol] such as that marketed under the trademark MIXXIM BB/100 by Fairmount Chemical, or micronized in dispersed form thereof such as that were marketed under the trademark TINOSORB M by Ciba Specialty Chemicals Corp. (Tarrytown, NY), and solubilized 2,2'-methylene-bis-[6-(2H-benzotriazol-2-yl)-4-(methyl)phenol] such as that marketed under the trademark MIXXIM BB/200 by Fairmount Chemical.

Typically combinations of one of more of these sunscreens are used.

The dibenzoyl methane derivatives other than avobenzone are described, for example, in FR 2,326,405, FR 2,440,933 and EP 114,607.

Other dibenzoyl methane sunscreens other than avobenzone include (whether singly or in any combination):

2-methyldibenzoylmethane;
4-methyldibenzoylmethane;
4-isopropyldibenzoylmethane;
4-tert-butyldibenzoylmethane;
2,4-dimethyldibenzoylmethane;
2,5-dimethyldibenzoylmethane;
4,4'-diisopropyldibenzoylmethane;
4,4'-dimethoxydibenzoylmethane;
2-methyl-5-isopropyl-4'-methoxydibenzoylmethane;
2-methyl-5-tert-butyl-4'-methoxydibenzoylmethane;
2,4-dimethyl-4'-methoxydibenzoylmethane; and
2,6-dimethyl-4-tert-butyl-4'-methoxydibenzoylmethane.

Additional sunscreens that can be used are described in pages 2954-2955 of the International Cosmetic Ingredient Dictionary and Handbook ($9^{th}$ ed. 2002).

The compositions of the present invention may further comprise at least one suitable (e.g., cosmetically or dermatologically acceptable) additive or adjuvant, including, for example, coloring agents (e.g., pigments and dyestuffs), antioxidants, essential oils, preserving agents, fragrances, fillers, pasty fatty substances, waxy fatty substances, neutralizing agents, and polymers, e.g., lipo-soluble polymers.

The compositions of the invention may also be optionally thickened with an aqueous-phase thickener or gelled with a gelling agent and/or containing ingredients soluble in water. Gelling agents that may be mentioned, for example, include crosslinked acrylates (e.g. Carbopol 982), hydrophobically-modified acrylates (e.g. Carbopol 1382); polyacrylamides such as, for example, the crosslinked copolymers sold under the names Sepigel 305 (CTFA name: (polyacrylamide/C13-C14 isoparaffin/Laureth 7) or Simulgel 600 (CTFA name: acrylamide/sodium acryloyldimethyltaurate copolymer/isohexadecane/polysorbate 80) by SEPPIC; 2-acrylamido-2-methylpropanesulphonic acid polymers and copolymers, that are optionally crosslinked and/or neutralized, for instance the poly(2-acrylamido-2-methylpropanesulphonic acid) sold by the company Hoechst under the trade name "Hostacerin AMPS" (CTFA name: ammonium polyacryldimethyltauramide); cellulose derivatives such as hydroxyethylcellulose, sodium carboxymethylcellulose, hydroxypropyl methylcellulose, hydroxypropyl cellulose, ethyl cellulose and hydroxymethyl cellulose; polysaccharides and gums, e.g., natural gums such as xanthan gum, sclerotium, carrageenan and pectin; and mixtures thereof. Amounts of the thickener may range from about 0.0001% to about 5%, preferably from about 0.001% to about 1%, and more preferably from about 0.01% to about 0.5% by weight of the cosmetic composition.

Examples of preservatives include alkyl para-hydroxybenzoates, wherein the alkyl radical has from 1, 2, 3, 4, 5 or 6 carbon atoms and preferably from 1 to 4 carbon atoms e.g., methyl para-hydroxybenzoate (methylparaben), ethyl para-hydroxybenzoate (ethylparaben), propyl para-hydroxybenzoate (propylparaben), butyl para-hydroxybenzoate (butylparaben) and isobutyl para-hydroxybenzoate (isobutylparaben). Mixtures of preservatives may certainly be used, e.g., the mixture of methyl-paraben, ethylparaben, propylparaben and butylparaben sold under the name Nipastat by Nipa, and the mixture of phenoxyethanol, methylparaben, ethylparaben, propylparaben and butylparaben sold under the name Phenonip, also by Nipa.

In embodiments where the cosmetic compositions are colored due to the presence of at least one pigment, the pigment is preferably treated, e.g., with an amino acid. Treated pigments are known in the art. See, e.g., U.S. Pat. No. 5,843,417. For example, pigments treated with silicones are described in U.S. Pat. No. 4,574,082, and pigments treated with amino acids are described in U.S. Pat. No. 4,606,914. Treated pigments are commercially available from U.S. Cosmetics Corp., a distributor of Miyoshi Kasei (Japan) (e.g., pigments treated with a vegetable-derived amino acid such as disodium stearoyl glutamate, aluminum oxide and optionally titanium dioxide).

Fillers that may be used in the compositions of the invention include silica powder; talc; polyamide particles and especially those sold under the name Orgasol by the company Atochem; polyethylene powders; microspheres based on acrylic copolymers, such as those based on ethylene glycol dimethacrylate/lauryl methacrylate copolymer sold by the company Dow Corning under the name Polytrap; expanded powders such as hollow microspheres and especially the microspheres sold under the name Expancel by the company Kemanord Plast or under the name Micropearl F 80 ED by the company Matsumoto; powders of natural organic materials such as crosslinked or noncrosslinked corn starch, wheat starch or rice starch, such as the powders of starch crosslinked with octenyl succinate anhydride, sold under the name Dry-Flo by the company National Starch; silicone resin microbeads such as those sold under the name Tospearl by the company Toshiba Silicone; clays (bentone, laponite, saponite, etc.) and mixtures thereof. These fillers may be present in amounts ranging from 0% to 20% by weight and preferably from 1% to 10% by weight relative to the total weight of the composition.

The amounts of these various adjuvants are those conventionally used in the cosmetics field. Generally, the amounts range from 0.01% to 20% relative to the total weight of the composition. Depending on their nature, these adjuvants may be introduced into the oil phase or the aqueous phase.

The composition can be packaged in a suitable container. The choice of container may depend upon the viscosity and intended use of the composition by the consumer. For example, a lotion or fluid cream can be packaged in a bottle or a roll-ball applicator, or a capsule, or a propellant-driven aerosol device or a container fitted with a pump suitable for finger operation. When the composition is a cream, it can simply be stored in a non-deformable bottle or squeeze container, such as a tube or a lidded jar.

The invention will be further described by reference to the following examples. These examples are provided for purposes of illustration only, and are not intended to be limiting unless otherwise specified.

EXAMPLE 1

Moisturizing Face Cream

| Phase | Ingredient | % |
|---|---|---|
| A1 | Deionized Water | Q.S. |
|  | Carbomer | 0.100 |
| A2 | Glycerin | 5.000 |
|  | Preservative | 0.5 |
|  | Active | 2.500 |
| B | Hydrogenated Polyisobutene (liquid) | 18.0 |
|  | Arlatone 2121 | 1.000 |
|  | Glyceryl Stearate | 4.500 |
|  | PEG-100 Stearate | 1.500 |
|  | Preservative | 0.5 |
| C | Deionized Water | 5.000 |
|  | Triethanolamine | 0.070 |
|  | TOTAL | 100.000 |

To prepare phase A1, the carbomer was slowly dispersed in water at room temperature to ensure absence of gel bodies. Once the carbomer was completely hydrated, the dispersion was heated to 75° C. The ingredients comprising phase A2 were added to the dispersion, one by one, with mixing in between each addition, all while maintaining constant temperature. Phase B ingredients were mixed separately at 85° C. while stirring. Phase B ingredients were then added to the dispersion with mixing for two minutes, followed by addition of pre-mixed phase C ingredients, while mixing for 5 minutes. Microscopic analysis was conducted at this point to determine uniformity and particle size. Homogenization was stopped, and the dispersion was cooled.

EXAMPLE 2

Cream

| Phase | | % |
|---|---|---|
| A1 | Deionized Water | 57.060 |
|  | Carbomer | 0.100 |
| A2 | Glycerin | 5.000 |
|  | Preservative | 0.5 |
|  | Active | 2.500 |
| B | Hydrogenated Polyisobutene | 18.0 |
|  | Sorbitan Stearate (and) Sucrose Cocoate | 1.000 |
|  | Cetearyl Alcohol | 1.000 |
|  | PEG-75 Stearate (and) Steareth-20 | 6.000 |
|  | Preservative | 0.5 |
|  | Fruit extracts | 0.030 |
|  | Vitamin | 1.500 |
|  | Vitamin | 0.090 |
| C | Deionized Water | 5.000 |
|  | Triethanolamine | 0.070 |
| D | Vitamin | 0.0300 |
| E | Deionized Water | 1.500 |
|  | Hydrolyzed Wheat Protein | 0.030 |
|  | TOTAL | 100.000 |

To prepare phase A1, the carbomer was slowly dispersed in water at room temperature to ensure absence of gel bodies. Once the carbomer was completely hydrated, the dispersion was heated to 75° C. The ingredients comprising phase A2 were added to the dispersion, one by one, with mixing in between each addition, all while maintaining constant temperature. Phase B ingredients were mixed separately at 85° C. while stirring. Phase B ingredients were then added to the dispersion with mixing for two minutes, followed by addition of pre-mixed phase C ingredients, while mixing for 5 minutes. Microscopic analysis was conducted at this point to determine uniformity and particle size. Homogenization was stopped, and the dispersion was cooled. Phase D ingredients were added at a temperature less than 45° C. Phase E ingredients were pre-mixed until the protein was dissolved, and then added to the dispersion at a temperature less than 45° C., followed by cooling to a temperature of 30° C.

All publications cited in the specification, both patent publications and non-patent publications, are indicative of the level of skill of those skilled in the art to which this invention pertains. All these publications are herein incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A cosmetic composition, comprising water, at least one non-polar and/or polar oil, and an emulsification system comprising a polyoxyethylene oxide C12-C24 fatty acid ester; a sucrose fatty acid ester of vegetable origin, a glyceryl C12-C24 fatty acid ester, and a sorbitan C12-C 24 fatty acid ester, wherein the ratio of said polyoxyethylene oxide C12-24 fatty acid ester to said sucrose fatty acid ester of vegetable origin is from about 5:1 to about 12:1, and wherein the combined amount of said glyceryl C12-C24 fatty acid ester and said sorbitan C12-24 fatty acid ester is from 2% to about 9%, said ratio and said amount being based on the total weight of said composition.

2. The composition of claim 1, wherein said polyoxyethylene oxide comprises polyethylene glycol (PEG) 75.

3. The composition of claim 1, wherein said polyoxyethylene oxide comprises PEG 100.

4. The composition of claim 1, wherein said C12-C24 fatty acid is stearic acid.

5. The composition of claim 1, wherein said polyoxyethylene oxide C12-C24 fatty acid comprises PEG 75 stearate.

6. The composition of claim 1, wherein said polyoxyethylene oxide C12-C24 fatty acid comprises PEG 100 stearate.

7. The composition of claim 1, wherein said sucrose fatty acid ester of vegetable origin comprises sucrose cocoate.

8. The composition of claim 1, wherein said sucrose fatty acid ester of vegetable origin comprises sucrose ricinoleate.

9. The composition of claim 1, comprising a glyceryl C12-C24 fatty acid ester.

10. The composition of claim 9, wherein said glyceryl C12-C24 fatty acid ester is glyceryl stearate.

11. The composition of claim 1, comprising a sorbitan C12-C24 fatty acid ester.

12. The composition of claim 11, wherein said sorbitan C12-C24 fatty acid ester is sorbitan stearate.

13. The composition of claim 1, comprising PEG 75 stearate, sucrose cocoate and glyceryl stearate.

14. The composition of claim 1, comprising PEG 100 stearate, sucrose cocoate and glyceryl stearate.

15. The composition of claim 1, comprising PEG 75 stearate, sucrose cocoate and sorbitan stearate.

16. The composition of claim 1, comprising PEG 100 stearate, sucrose cocoate and sorbitan stearate.

17. The composition of claim 1, comprising PEG 75 stearate, sucrose cocoate, sorbitan stearate and glyceryl stearate.

18. The composition of claim 1, comprising PEG 100 stearate, sucrose cocoate, sorbitan stearate and glyceryl stearate.

19. The composition of claim 1, comprising sorbitan stearate and sucrose cocoate.

20. The emulsification system of claim 1, comprising PEG 75 stearate and glyceryl stearate.

21. The composition of claim 1, which is in the form of a cream.

22. The composition of claim 1, which is in the form of a lotion.

23. The composition of claim 1, which is in the form of an oil-in-water emulsion.

24. The composition of claim 1, which is in the form of an water-in-oil emulsion.

25. The composition of claim 1, which is in the form of a multiple emulsion.

26. The composition of claim 1, which comprises at least one polar oil.

27. The composition of claim 26, wherein the polar oil comprises an alkyl benzoate.

28. The composition of claim 27, wherein the alkyl benzoate comprises a C12-C15 alkyl benzoate.

29. The composition of claim 1, which comprises at least one non-polar oil.

30. The composition of claim 29, wherein the non-polar oil comprises a polyisobutene.

31. The composition of claim 30, wherein the polyisobutene comprises a hydrogenated polyisobutene.

32. The composition of claim 1, comprising at least one polar oil and at least one non-polar oil.

33. The composition of claim 1, wherein said at least one polar and/or non-polar oil is present in said composition in an amount of about 18% by weight of said composition.

34. The composition of claim 1, wherein said emulsification system is present in said composition in an amount of about 2% to about 15% by weight of said composition.

35. The composition of claim 1, wherein said polyoxyethylene oxide C12-C24 fatty acid ester is present in said composition in an amount of about 0.25% to about 6% by weight of said composition.

36. The composition of claim 35, wherein the amount of said polyoxyethylene oxide C12-C24 fatty acid ester is about 3% to about 7% of said composition.

37. The composition of claim 1, wherein said sucrose C12-C24 fatty acid ester is present in said composition in an amount of about 0.05% to about 0.5% of said composition.

38. The composition of claim 37, wherein the amount of said sucrose C12-C24 fatty acid ester is about 0.1% to about 0.3%.

39. The composition of claim 1, which comprises said glyceryl C12-C24 fatty acid ester and said sorbitan C12-C24 fatty acid ester, and wherein said polyoxyethylene oxide C12-C24 fatty acid ester and said glyceryl C12-C24 fatty acid ester are present in an amount of about 3% to about 10% by weight of said composition.

40. The composition of claim 1, which comprises said glyceryl C12-C24 fatty acid ester and said sorbitan C12-C24 fatty acid ester, and wherein said sucrose C12-C24 fatty acid ester and said sorbitan C12-C24 fatty acid ester are present in an amount of about 0.5% to about 1.5% by weight of said composition.

41. The composition of claim 40, wherein the amount of said sucrose C12-C24 fatty acid ester and said sorbitan C12-C24 fatty acid ester is about 0.7% to about 1.2% by weight of said composition.

42. The composition of claim 1, further comprising a dermatological active agent.

43. The composition of claim 42, wherein said agent is selected from the group consisting of moisturizers, free-radical scavengers, keratolytic agents, vitamins, anti-elastase and anti-collagenase agents, peptides, fatty acid derivatives, steroids, trace elements, bleaching agents, extracts of algae and of planktons, sunscreens, enzymes and coenzymes, flavonoids and ceramides, α-hydroxy acids and mixtures thereof.

44. The composition of claim 1, further comprising a sunscreen agent.

45. The composition of claim 1, further comprising a thickener.

46. The composition of claim 1, further comprising a gelling agent.

47. The composition of claim 1, further comprising a cosmetically or dermatological acceptable adjuvant or additive.

48. A method of applying make-up to keratinous tissue, comprising applying the cosmetic composition of claim 1 to the keratinous tissue.

49. The method of claim 48, wherein the keratinous tissue comprises skin.

* * * * *

UNITED STATES PATENT AND TRADEMARK OFFICE
CERTIFICATE OF CORRECTION

PATENT NO. : 8,158,136 B2  
APPLICATION NO. : 10/920615  
DATED : April 17, 2012  
INVENTOR(S) : Hani Fares et al.

Page 1 of 1

It is certified that error appears in the above-identified patent and that said Letters Patent is hereby corrected as shown below:

In the Specifications:

Column 4, line 46, "a-hydroxy" should read -- α-hydroxy --.

Signed and Sealed this  
Twenty-third Day of July, 2013

Teresa Stanek Rea  
*Acting Director of the United States Patent and Trademark Office*